United States Patent [19]

Baumgarth et al.

[11] 4,209,444
[45] Jun. 24, 1980

[54] NEW PROSTAGLANDIN-LIKE DIKETALS

[75] Inventors: Manfred Baumgarth; Dieter Orth; Hans-Eckart Radunz; Reinhard Lissner; Jürgen Maisenbacher, all of Darmstadt, Fed. Rep. of Germany

[73] Assignee: Merck Patent Gesellschaft Mit Beschrankter Haftung, Darmstadt, Fed. Rep. of Germany

[21] Appl. No.: 855,591

[22] Filed: Nov. 29, 1977

[30] Foreign Application Priority Data

Nov. 29, 1976 [DE] Fed. Rep. of Germany ....... 2654113

[51] Int. Cl.² .......................................... C07C 177/00
[52] U.S. Cl. ..................... 260/338; 560/53; 560/55; 562/465
[58] Field of Search ................... 260/338; 560/53, 55; 562/465

[56] References Cited

PUBLICATIONS

Derwent Abstract 83555W/51, DT2524–326, 03.06.74.

Primary Examiner—Paul J. Killos
Attorney, Agent, or Firm—Millen & White

[57] ABSTRACT

Compounds of formula

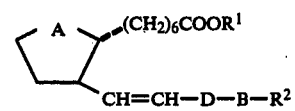

I their mirror images and racemic mixtures, and the physiologically acceptable salts thereof, wherein A and D each are ketalized carbonyl groups; B is —$CH_2$—, —$CH(CH_3)$—, —$C(CH_3)_2$—, —$CH_2CH_2$—, —$CH(CH_3)CH_2$—, —$C(CH_3)_2CH_2$— or —$CH_2O$—; $R^1$ is H or alkyl of 1-4 C-atoms; and $R^2$ is alkyl of 3 to 5 C-atoms, phenyl or phenyl substituted one to three times by F, Cl, $CF_3$, OH, $OCH_3$, $OC_2H_5$ or alkyl of 1 to 3 C-atoms inhibit aggregation and/or adhesion of thrombocytes.

13 Claims, No Drawings

NEW PROSTAGLANDIN-LIKE DIKETALS

SUMMARY OF THE INVENTION

An object of the present invention is the provision of new compounds which possess valuable pharmacological properties and can be employed for the preparation of medicaments.

Upon further study of the specification and appended claims, further objects and advantages of this invention will become apparent to those skilled in the art.

These objects have been attained in a composition aspect of the invention providing prostaglandin-like compounds of the formula I

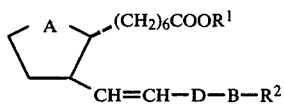

their mirror images and racemic mixtures, and the physiologically acceptable salts thereof, wherein A and D each are ketalized carbonyl groups; B is $—CH_2—$, $—CH(CH_3)—$, $—C(CH_3)_2—$, $—CH_2CH_2—$, $—CH(CH_3)CH_2—$, $—C(CH_3)_2CH_2—$ or $—CH_2O—$; $R^1$ is H or alkyl of 1–4 C-atoms; and $R^2$ is alkyl of 3 to 5 C-atoms, phenyl or phenyl substituted one to three times by F, Cl, $CF_3$, OH, $OCH_3$, $OC_2H_5$ or alkyl.

In another composition aspect, this invention provides a pharmaceutical composition which comprises an amount of a compound of formula I effective for inhibiting aggregation and/or adhesion of thrombocytes and a pharmaceutically acceptable adjuvant.

In a method of use aspect, this invention provides a method of inhibiting aggregation and/or adhesion of thrombocytes in mammals, including humans, which comprises administering an amount of a compound of Formula I effective for such inhibition.

DETAILED DISCUSSION

In the formula herein, an α-positioned bond is indicated by a dotted line and a β-positioned bond by a solid liner. Bonds which may be in the α- or β-positions are indicated by a wavy line.

The compounds of formula I contain at least 2 asymmetrical C-atoms. However, additional centers of asymmetry can also occur, for example, when $R^2$ is a branched alkyl radical with 3–5 C-atoms. Therefore the compounds of formula I can occur in a plurality of stereoisomeric forms; as a rule, they are present as racemic mixtures, together with their mirror images.

Besides the individual racemates and racemic mixtures, the scope of the invention also includes the optically-active isomers of the compounds of formula I, as well as their mirror images.

In formula I, $R^1$ is, besides hydrogen, especially an alkyl radical with 1–4 C-atoms. These alkyl radicals are preferably unbranched. Especially suitable is the ethyl radical. Other suitable $R^1$ alkyl radicals include: methyl, propyl, isopropyl, n-butyl, sec-butyl, isobutyl or tert-butyl.

$R^2$ is preferably an alkyl radical with 3–5 C-atoms, especially an unbranched alkyl radical with 3–5 C-atoms, such as propyl, butyl or pentyl. Other suitable $R^2$ alkyl radicals include: isopropyl, isobutyl, isopentyl, sec-butyl, tert-butyl, pent-2-yl, pent-3-yl, 2-methylbutyl or neopentyl.

$R^2$ can also be phenyl or phenyl substituted one, two or three times by F, Cl, $CF_3$, OH, $OCH_3$, $OC_2H_5$, alkyl with 1–3 C-atoms or combinations thereof. When $R^2$ is a substituted phenyl radical, it is preferably mono-substituted, especially in the m- or p-position, but also in the o-position. Therefore, $R^2$ is preferably also m-fluorophenyl, p-fluorophenyl, m-chlorophenyl, p-chlorophenyl, m-hydroxyphenyl, p-hydroxyphenyl, m-methoxyphenyl, p-methoxyphenyl, m-ethoxyphenyl, p-ethoxyphenyl, m-trifluoromethylphenyl, p-trifluoromethylphenyl, o-tolyl, m-tolyl, p-tolyl, p-ethylphenyl or p-isopropylphenyl; but for example, 2,4-dichloro-, 3,4-dichloro, -dichloro, 2,4-dimethyl-, 3,4-dimethyl-, 2,4-dimethoxy-, 2,3-dimethoxy-, 2,4,6-trimethyl- and 3,4,5-trimethoxyphenyl are also suitable.

A and D can be the same or different and each is a ketalised carbonyl group. Suitable such groups include open ketal groups having a total of up to 5 C-atoms and cyclic ketal groups having a total of up to 6 C-atoms. Preferred ketals are the dimethylketals, the diethylketals and ethylene-ketals. Suitable A and D groups include: dialkoxymethylene groups having a total of up to 5 C-atoms, e.g. dimethoxymethylene, diethoxymethylene, ethoxymethoxymethylene; optionally alkyl substituted 1,3-dioxolan-2,2-diyl and 1,3-dioxan-2,2-diyl groups having a total of up to 6 C-atoms e.g. 1,3-dioxolan-2,2-diyl, 4-methyl-1,3-dioxolan-2,2-diyl and 1,3-dioxan-2,2-diyl. Those compounds of formula I are preferred in which A and D are the same.

B is preferably $—CH_2—$, $—CH_2CH_2—$ or $—CH_2O—$. However, in addition, B can also be $—CH(CH_3)—$, $—C(CH_2)_2—$, $—CH(CH_3)CH_2—$ or $—C(CH_3)_2CH_2—$. The combination of $BR^2$ is preferably an unbranched alkyl radical with 4–7 C-atoms, especially with 5 C-atoms.

Especially preferred are those compounds of formula I in which at least one of $R^1$, $R^2$, A, B and D is one of the preferred embodiments mentioned above. Some of these preferred groups of compounds can be characterized by the following partial formula Ia to Ii which otherwise correspond to formula I, and in which the symbols not explicitly defined have the same meanings as for formula I: in Ia A and D are the same and are dimethoxymethylene, diethoxymethylene or 1,3-dioxolan-2,2-diyl;

in Ib B is methylene or ethylene and $R^2$ is butyl or pentyl;

in Ic B is methylene or $—CH_2O—$ and $R^2$ is phenyl, m-chlorophenyl, p-chlorophenyl, m-fluorophenyl, m-trifluoromethylphenyl, m-methoxyphenyl or p-methoxyphenyl;

in Id A and D are the same and are dimethoxymethylene, diethoxymethylene or 1,3-dioxolan-2,2-diyl; B is methylene or ethylene and $R^2$ is butyl or pentyl;

in Ie A and D are the same and are 1,3-dioxolan-2,2-diyl; B is methylene or ethylene and $R^2$ is butyl or pentyl;

in If A and D are the same and are 1,3-dioxolan-2,2-diyl; B is methylene and $R^2$ is butyl;

in Ig A and D are the same and are dimethoxymethylene, diethoxymethylene or 1,3-dioxolan-2,2-diyl; B is methylene or $—CH_2O—$ and $R^2$ is phenyl, m-chlorophenyl, p-chlorophenyl, m-fluorophenyl, m-trifluoromethylphenyl, m-methoxyphenyl or p-methoxyphenyl;

in Ih A and D are the same and are dimethoxymethylene, diethoxymethylene or 1,3-dioxolan-2,2-diyl; B is $—CH_2O—$ and $R^2$ is phenyl, m-chlorophenyl, p- chlorophenyl, m-fluorophenyl, m-trifluoromethylphenyl, m-methoxyphenyl or p-methoxyphenyl;

in Ii A and D are the same and are 1,3-dioxolan-2,2-diyl; B is —CH$_2$O— and R$^2$ is phenyl, m-chlorophenyl, p-chlorophenyl, m-fluorophenyl, m-trifluoromethylphenyl, m-methoxyphenyl or p-methoxyphenyl.

The preparation of the compounds of formula I can be accomplished by per se known methods, such as are described in the literature (e.g. in standard works, such as Houben-Weyl, Methoden der Organische Chemie, Georg-Thieme-Verlag, Stuttgart; or Organic Reactions, John Wiley & Sons, Inc., New York), under the conventional reaction conditions known to be suitable for such reactions. Thus, many known variants not mentioned in detail herein, can also be used.

Such conventional preparative methods include the following:

(1) reacting a compound of formula II

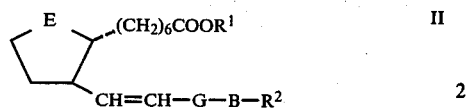

wherein E and G are free or ketalised carbonyl groups and at least one of the residues E and G is a free carbonyl group, and B, R$^1$ and R$^2$ are as defined above, with a ketalising agent.

(2) converting a compound of formula I wherein R$^1$ is H, into another compound of formula I wherein R$^1$ is alkyl with 1–4 C atoms, by reaction with an esterifying agent;

(3) converting a compound of formula I wherein R$^1$ is alkyl with 1–4 C atoms, into another compound of formula I wherein R$^1$ is H by reaction with a saponifying agent; and/or;

(4) converting a compound of formula I wherein R$^1$ is H into one of its physiologically acceptable salts by reaction with a base, or liberating such a compound from one of its salts by reaction with an acid.

The starting materials of the formula II are, in part, known, and in part new. As described below in detail, they can be prepared according to methods, known per se, if desired in situ, i.e., in such a manner that they are not isolated from the reaction mixture but rather are immediately reacted further to produce the compounds of formula I.

For formula II, R$^1$, R$^2$ and B are the same as for formula I, especially those stated to be preferred. E and G are free or ketalised carbonyl groups, and at least one of E and G must be a free carbonyl group. Suitable ketalised carbonyl groups, for E and G are those mentioned above for A and D. Particularly useful are those compounds of formula II in which both groups E and G are free carbonyl groups.

The new compounds of formula II can be prepared by analogy to techniques used to prepare the known compounds of formula II according to standard methods known from the literature from known starting materials. For example, 7-(2-formyl-5-oxocyclopentyl)-heptanoic acid or its lower alkyl esters of the formula Va

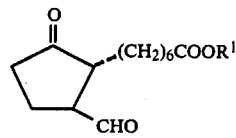

wherein R$^1$ is as defined above, can be reacted, e.g., with a dimethylphosphonate of the formula VI

wherein R$^2$ and B are as defined above. The phosphonates of formula VI are known, for example, from published German Pat. No. P 25 08 995, especially Example 1. New phosphonates of formula VI can be prepared according to the conventional methods disclosed therein.

Moreover, ketalised 7-(2-formyl-5-oxo-cyclopentyl)-heptanoic acids or their esters of the formula Vb

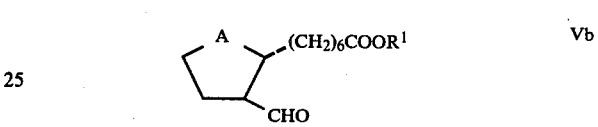

wherein R$_1$ and A are as defined above, can be reacted with a phosphonate of the formula VI to produce one of the desired starting compounds of the formula II in which the carbonyl group of the cyclopentane ring is already ketalised. The compounds of the formula Vb are, in part, known, for example, from Tetrahedron Letters, 1972, 3815, or can be prepared by analogy to the methods disclosed therein.

Finally, it is also possible to react 7-(2-formyl-5-hydroxycyclopentyl)-heptanoic acid or its esters of the formula Vc

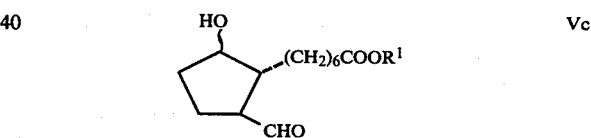

wherein R$^1$ is as defined above, with a phosphonate of the formula VI, either to also oxidize the resultant cyclopentanol directly to a compound of formula II with E=G= a free carbonyl group, or initially to also react with a ketalising agent to produce a compound of formula VII

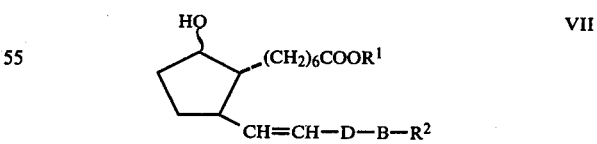

wherein R$^1$, R$^2$, B and D are as defined above, and then to convert the compounds of formula VII, by treatment with an oxidizing agent, into a starting compound of formula II.

Known starting compounds of formula II are described, for example, in published German Pat. No. P 22 31 244, especially Example 3 (E=G=a free carbonyl group) and in published German Pat. No. P 23 53 788 (especially the compound of the formula III therein), in which are mentioned the compounds of formula II with E=1,3-dioxolan-2,2-diyl and G=a free carbonyl group.

Suitable ketalising agents, include lower monohydroxy alkanols, e.g., methanol or ethanol and dihydroxy alkanols with up to 5 C-atoms. Preferred dihydroxy alkanols with up to 5 C-atoms are especially ethyleneglycol, propane-1,3-diol and 2,2-dimethylpropane-1,3-diol but also include propane-1,2-diol and butane-2,3-diol. In addition, suitable diols also include, butane-1,2-diol, 2-methylpropane-1,2-diol, 2-methylpropane-1,3-diol and butane-1,3-diol. Other suitable ketalising agents include trimethyl or triethyl ortho esters, preferably trimethyl orthoformate or triethyl orthoformate. Moreover, ketals of lower ketones, especially of acetone or of butanone (which can be represented, e.g., as $CH_3ACH_3$ or $C_2H_5ACH_3$) are also suitable ketalising agents. For example, these include acetone dimethyl ketal, acetone diethyl ketal, 2,2-dimethyl-1,3-dioxolan, 2-ethyl-2-methyl-1,3-dioxolan, 2,2-dimethyl-1,3-dioxan and 2,2,5,5-tetramethyl-1,3-dioxan.

The reaction of a compound of formula II with one of the above-mentioned ketalising agents is preferably conducted in the presence of acid catalysts. Suitable acid catalysts include mineral acids, such as hydrochloric acid or sulphuric acid, Lewis acids, such as boron trifluoride, and also strong organic acids, especially sulphonic acids, such as methanesulphonic acid, ethanesulphonic acid, benzenesulphonic acid or p-toluenesulphonic acid.

The reaction of a compound of formula II with a ketalising agent can be carried out with or without solvent. If one of the above-mentioned mono- or dihydroxy alcohols is used as ketalising agent, then it is especially advantageous to use an excess of the alcohol as the solvent. Since the ketalisation of is an equilibrium reaction, it is expedient to continuously remove the water being formed from the reaction mixture. This can be done, for example, by the addition of benzene to the reaction mixture and azeotropic distillation. If, an ortho ester or a ketal of a lower ketone is used as ketalising agent, the reaction is a transketalisation in which no water is formed. Also for the latter variant, it is advantageous to employ an excess of ketalising agent as the solvent. When an ortho ester is used, it is especially advantageous to additionally use methanol or ethanol as solvent. In the transketalisation with a ketal of a lower ketone, it is advantageous to conduct the reaction so that the lower ketone being formed is continuously removed from the reaction mixture by distillation. Generally, the ketalisations are performed at an elevated temperature, preferably at the boiling temperature of the reaction mixture. Suitable reaction times are between about 4 hours and about 20 hours.

Compounds of formula I wherein $R^1$ is H can be conventionally esterified with an esterifying agent. Suitable esterifying agents, include alcohols with up to 4 C-atoms, preferably in the presence of an inorganic or organic acid, such as HCl, HBr, HI, $H_2SO_4$, $H_3PO_4$, trifluoroacetic acid, or a sulphonic acid, such as benzenesulphonic acid or p-toluenesulphonic acid, or of an acidic ion exchanger; diazoalkanes with up to 4 C-atoms, preferably diazomethane; olefins (e.g. isobutylene), preferably in the presence of acidic catalysts (e.g. $ZnCl_2$, $BF_3$, $H_2SO_4$, arylsulphonic acid, pyrophosphoric acid, boric acid, oxalic acid); alkyl halides with up to 4 C-atoms, preferably bromides, such as ethyl, propyl, isopropyl or butyl bromide, but also the corresponding chlorides or iodides; carboxylic acid or sulphonic acid alkyl esters, wherein the acid residue can be as desired and the alkyl radical contains up to 4 C-atoms, preferably methyl, ethyl, propyl, isopropyl or butyl acetate, formate, methylsulphonate, ethylsulphonate, or p-toluenesulphonate; and espcially also dialkyl sulphuric acid esters with up to 4 C-atoms, such as dimethyl sulphate or diethyl sulphate.

The esterification is conducted in a suitable inert, preferably anhydrous, solvent, for example, an ether, such as diethyl ether or THF; an alcohol, preferably a lower branched or unbranched alkanol, such as methanol, ethanol, propanol, isopropyl alcohol or butanol; a hydrocarbon, such as petroleum ether, hexane, benzene or toluene; or mixtures of these solvents, at temperatures between about $-10°$ and $85°$ C. Suitable reaction times are generally between 30 minutes and 24 hours. Because of the high sensitivity of the ketal group towards aqueous acids, care is to be taken that the solvent is completely dry. However, even then, undesired side reactions cannot be completely excluded and transketalisation can occur. Therefore, the esterification is best carried out using diazoalkanes.

If methanol or ethanol is used as the ketalising agent, the corresponding esters of formula I ($R^1=CH_3$ or $C_2H_5$) are generally produced from the compounds of formula II ($R^1=H$).

The saponification of compounds of formula I ($R^1=$alkyl with 1-4 C-atoms) into other compounds of formula I ($R^1=H$), is conducted according to per se known methods by reaction with aqueous bases, e.g. aqueous solutions of alkali metal hydroxides or carbonates, such as NaOH, KOH or $Na_2CO_3$.

The free carboxylic acids of formula I ($R^1=H$) can be converted, by reaction with a corresponding base, into one of their physiologically acceptable metal or ammonium salts. Suitable salts, especially include sodium, potassium, magnesium, calcium and ammonium salts, and also substituted ammonium salts, such as the dimethyl and diethyl ammonium, monoethanol, diethanol and triethanol ammonium, cyclohexyl ammonium, dicyclohexyl ammonium and dibenzyl ethylene diammonium salts. Conversely, acids of formula I can be liberated from their metal and ammonium salts by treatment with acids, especially mineral acids, such as hydrochloric or sulphuric acid. Because of the acid sensitivity of the ketal groups, conditions under which the reaction mixture reacts acidically must be avoided. Therefore, more expediently, the solution of the salt can be titrated with acid up to the equivalence point.

The compounds of the formula I are derived from prostanoic acid, the systematic name of which is 7-(2-octylcyclopentyl)-heptanoic acid. The compounds of formula I especially include derivatives of 13-prostenoic acid, i.e., 7-(2-(1-trans-octenyl)-cyclopentyl)-heptanoic acid. Such compounds of formula I are, characterized herein as derivatives of 13-prostenoic acid wherein the double bond has the trans configuration when not expressly stated otherwise.

As mentioned above, the compounds of formula I in general have several centers of asymmetry, but always at least two. Therefore, they are generally obtained as mixtures of different stereoisomeric forms, i.e. as racemates or, as a rule, as mixtures of racemates. Since various racemates are diastereomeric to one another, they can be isolated from their mixtures on the basis of their differing physical properties, and can be obtained in pure form, for example, by recrystallization from suitable solvents (where instead of the compounds themselves, well-crystallizing derivatives can be used); by distillative separation; but especially by chromatographic methods, including not only adsorption chromatography or partition chromatography but also mixed forms.

The racemates can be separated into their optical antipodes by any of a plurality of known methods, disclosed in the literature. The method of chemical separation is preferred. By this method, diastereomers are formed from racemic mixtures, by reaction with an optically-active adjuvant.

Thus, it is possible to react an optically-active base with the carboxyl group of a compound of formula I. For example, diastereomeric salts of the compound of formula I wherein $R^1$ is H can be reacted with optically-active amines, such as quinine, brucine, 1-phenylethylamine, 1-(α-naphthyl)ethylamine etc., or basic amino acids, such as lysine, arginine etc. In a similar manner, ester diastereomers can be prepared by esterification of compounds of formula I ($R^1 = H$) with optically-active alcohols, such as borneol, menthol or octan-2-ol. The difference in the solubility of the diastereomeric salts or esters obtained permits the selective crystallization of one form and the regeneration of the respective optically-active compounds from the mixture.

Furthermore, it is, of course, also possible to obtain optically-active compounds directly from the afore-described methods by employing optically-active starting materials.

It has been found that the prostaglandin-like compounds of formula I possess valuable pharmacological properties. In particular, they exhibit thrombocyte aggregation-inhibiting and/or adhesion-inhibiting properties which can be demonstrated, for example, by analogy with the method disclosed by Born, in Nature (London), 194, 927 (1962). Therefore, the compounds of formula I can be employed as medicaments.

Moreover, they also can be used as intermediates in the preparation of other medicaments, i.e., other prostaglandin-like compounds. Thus, for example, by treatment with dilute aqueous acids, preferably aqueous mineral acids, such as HCl or $H_2SO_4$, but also with aqueous organic acids, such as oxalic acid or p-toluene-sulphonic acid, it is possible to convert these into the diketones of formula III

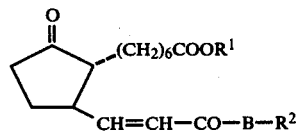

III wherein B, $R^1$ and $R^2$ are as defined above, their mirror images and/or racemic mixtures. The compounds of the formula III can, in turn, be converted, e.g. by reaction with reducing agents, such as sodium borohydride, into the dihydroxy compounds of formula IV

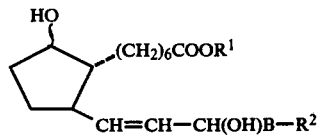

IV wherein B, $R^1$ and $R^2$ are also as defined above, their mirror images and/or racemic mixtures. The compounds of formula IV and their properties are known from the published German Pat. No. 25 08 995; they have e.g. blood pressure reducing activities. The hydrolysis of compounds of formula I to compounds of formula III by aqueous oxalic acid can be effected under the same conditions as given in J. Chem. Soc., 364 (1962) for the hydrolysis of an enol ether. The reduction of a compound of formula III to a compound of formula IV can be achieved with $NaBH_4$ in analogy to example 81 of the published German Pat. No. 25 08 995.

When used as medicaments, the new compounds of formula I can be mixed with at least one pharmaceutically conventional solid, liquid and/or semi-liquid carrier or adjuvant material.

Such mixtures can be used as medicaments in human and veterinary medicine. Suitable carrier materials include those organic or inorganic materials which are suitable for parenteral, enteral (e.g. oral) or topical administration and which do not react with the new compounds of formula I, for example, water, vegetable oils, benzyl alcohols, polyethylene glycols, glycerol triacetate, gelatine, lactose, starch, magnesium stearate, talc, vaseline, cholesterol. For oral administration, tablets, dragees, capsules, syrups, juices, or drops are suitable; for rectal administration suppositories are suitable; for parenteral administration solutions, preferably oily or aqueous solutions; suspensions, emulsions or implants are suitable; and for topical use, salves, creams or powders are suitable.

The new compounds cna also be lyophilized and the resultant lyophilizates used e.g. for the production of injection preparations. The described compositions can optionally be sterilized or mixed with adjuvants, such as lubricating, preserving, stabilizing or wetting agents, emulsifiers, salts which influence the osmotic pressure, buffer substances, coloring, flavoring and/or aroma generating materials. If desired, the compositions can also contain one or more additional active materials, e.g. one or more vitamins.

The compounds of formula I are preferably administered in a dosage of 0.01 to 200 mg, especially of 0.1 to 100 mg, especially of 0.5 to 50 mg per dosage unit. The suitable dosage is dependent upon the species treated, the form of administration and the purpose of the treatment, and can, therefore, be above or below the above-given values.

IR spectra (IR) are characterized by specification of the main bands (measured as a film). The NMR spectra (NMR) were measured in $CDCl_3$ against tetramethylsilane and are characterized by specification of the signals in ppm, wherein m=multiplet, q=quartet, t=triplet, d=doublet and s=singlet.

Each of the compounds of formula I mentioned in the following examples is especially suitable for the preparation of medicaments.

EXAMPLE 1

A mixture of 2 g of 9,9-ethylenedioxy-15-oxo-13-prostenoic acid ethyl ester, 100 ml of dry benzene, 10 ml of ethyleneglycol and 0.2 g of p-toluenesulphonic acid is boiled for 20 hours on a water separator. After cooling the mixture is diluted with 100 ml of diethyl ether and washed with aqueous $NaHCO_3$ solution and water. The organic phase is dried over $Na_2SO_4$ and the solvent is distilled. After chromatographic purification of the residue (silica gel/diisopropyl ether), 9,9;15,15-bis-(ethylenedioxy)-13-prostenoic acid ethyl ester is obtained.

IR: 1730 and 1460 cm$^{-1}$; NMR: 5.71 (q), 5.32 (d), 4.13 (q), 3.19 (m).

EXAMPLES 2–43

Analogously to Example 1, from the corresponding 9,9-ethylenedioxy-15-oxo-13-prostenoic acid derivatives of formula II, there are obtained, by reaction with ethyleneglycol, the following compound of formula I;

| Example | Compound of formula I |
|---|---|
| 2 | 9,9;15,15-bis-(ethylenedioxy)-16-methyl-13-prostenoic acid ethyl ester |
| 3 | 9,9;15,15-bis-(ethylenedioxy)16,16-dimethyl-13-prostenoic acid ethyl ester |
| 4 | 9,9;15,15-bis-(ethylenedioxy)-20-methyl-13-prostenoic acid ethyl ester |
| 5 | 9,9;15,15-bis-(ethylenedioxy)-20-ethyl-13-prostenoic acid ethyl ester |
| 6 | 9,9;15,15-bis-(ethylenedioxy)-16,20-dimethyl-13-prostenoic acid ethyl ester |
| 7 | 9,9;15,15-bis-(ethylenedioxy)-16,16-20-trimethyl-13-prostenoic acid ethyl ester |
| 8 | 9,9;15,15-bis-(ethylenedioxy)-16-methyl-20-ethyl-13-prostenoic acid ethyl ester |
| 9 | 9,9;15,15-bis-(ethylenedioxy)-16,16-dimethyl-20-ethyl-13-prostenoic acid ethyl ester |
| 10 | 9,9;15,15-bis-(ethylenedioxy)-17-phenyl-18,19,20-tris-nor-13-prostenoic acid ethyl ester |
| 11 | 9,9;15,15-bis-(ethylenedioxy)-17-p-fluorophenyl-18,19,20-tris-nor-13-prostenoic acid ethyl ester |
| 12 | 9,9;15,15-bis-(ethylenedioxy)-17-m-fluorophenyl-18,19,20-tris-nor-13-prostenoic acid ethyl ester |
| 13 | 9,9;15,15-bis-(ethylenedioxy)-17-p-chlorophenyl-18,19,20-tris-nor-13-prostenoic acid ethyl ester |
| 14 | 9,9;15,15-bis-(ethylenedioxy)-17-m-chlorophenyl-18,19,20-tris-nor-13-prostenoic acid ethyl ester |
| 15 | 9,9;15,15-bis-(ethylenedioxy)-17-o-chlorophenyl-18,19,20-tris-nor-13-prostenoic acid ethyl ester |
| 16 | 9,9;15,15-bis-(ethylenedioxy)-17-m-trifluoromethyphenyl-18,19,20-tris-nor-13-prostenoic acid ethyl ester |
| 17 | 9,9;15,15-bis-(ethylenedioxy)-17-p-hydroxyphenyl-18,19,20-tris-nor-13-prostenoic acid ethyl ester |
| 18 | 9,9;15,15-bis-(ethylenedioxy)-17-m-hydroxyphenyl-18,19,20-tris-nor-prostenoic acid ethyl ester |
| 19 | 9,9;15,15-bis-(ethylenedioxy)-17-p-methoxyphenyl-18,19,20-tris-nor-13-prostenoic acid ethyl ester |
| 20 | 9,9;15,15-bis-(ethylenedioxy)-17-m-methoxyphenyl-18,19,20-tris-nor-13-prostenoic acid ethyl ester |
| 21 | 9,9;15,15-bis-(ethylenedioxy)-17-p-ethoxyphenyl-18,19,20-tris-nor-13-prostenoic acid ethyl ester |
| 22 | 9,9;15,15-bis-(ethylenedioxy)-17-(2,4-dimethoxyphenyl)-18,19,20-tris-nor-13-prostenoic acid ethyl ester |
| 23 | 9,9;15,15-bis-(ethylenedioxy)-17-(2,4-dichlorophenyl)-18,19,20-tris-nor-13-prostenoic acid ethyl ester |
| 24 | 9,9;15,15-bis-(ethylenedioxy)-17-(3,4,5-trimethoxyphenyl)-18,19,20-tris-nor-13-prostenoic acid ethyl ester |
| 25 | 9,9;15,15-bis-(ethylenedioxy)-16-phenyl-17,18,19,20-tetrakisnor-13-prostenoic acid ethyl ester |
| 26 | 9,9;15,15-bis-(ethylenedioxy)-16-p-fluorophenyl-17,18,19,20-tetrakisnor-13-prostenoic acid ethyl ester |
| 27 | 9,9;15,15-bis-(ethylenedioxy)-16-m-fluorophenyl-17,18,19,20-tetrakisnor-13-prostenoic acid ethyl ester |
| 28 | 9,9;15,15-bis-(ethylenedioxy)-16-p-chlorophenyl-17,18,19,20-tetrakisnor-13-prostenoic acid ethyl ester |
| 29 | 9,9;15,15-bis-(ethylenedioxy)-16-m-chlorophenyl-17,18,19,20-tetrakisnor-13-prostenoic acid ethyl ester |
| 30 | 9,9;15,15-bis-(ethylenedioxy)-16-m-trifluoromethylphenyl-17,18,19,20-tetrakisnor-13-prostenoic acid ethyl ester |
| 31 | 9,9;15,15-bis-(ethylenedioxy)-16-m-hydroxyphenyl-17,18,19,20-tetrakisnor-13-prostenoic acid ethyl ester |
| 32 | 9,9;15,15-bis-(ethylenedioxy)-16-p-methoxyphenyl-17,18,19,20-tetrakisnor-13-prostenoic acid ethyl ester |
| 33 | 9,9;15,15-bis-(ethylenedioxy)-16-m-methoxyphenyl-17,18,19,20-tetrakisnor-13-prostenoic acid ethyl ester |
| 34 | 9,9;15,15-bis-(ethylenedioxy)-16-phenoxy-17,18,19,20-tetrakisnor-13-prostenoic acid ethyl ester |
| 35 | 9,9;15,15-bis-(ethylenedioxy)-16-p-fluorophenoxy-17,18,19,20--tetrakisonr-13-prostenoic acid ethyl ester |
| 36 | 9,9;15,15-bis-(ethylenedioxy)-16-m-fluorophenoxy-17,18,19,20-tetrakisnor-13-prostenoic acid ethyl ester |
| 37 | 9,9;15,15-bis-(ethylenedioxy)-16-p-chlorophenoxy-17,18,19,20-tetrakisnor-13-prostenoic acid ethyl ester |
| 38 | 9,9;15,15-bis-(ethylenedioxy)-16-m-chlorophenoxy-17,18,19,20-tetrakisnor-13-prostenoic acid ethyl ester |
| 39 | 9,9;15,15-bis-(ethylenedioxy)-16-m-trifluoromethylphenoxy-17,18,19,20-tetrakisonor-13-prostenoic acid ethyl ester |
| 40 | 9,9;15,15-bis-(ethylenedioxy)-16-m-hydroxyphenoxy-17,18,19,20-tetrakisnor-13-prostenoic acid ethyl ester |
| 41 | 9,9;15,15-bis-(ethylenedioxy)-16-p-methoxyphenoxy-17,18,19,20-tetrakisnor-13-prostenoic acid ethyl ester |
| 42 | 9,9;15,15-bis-(ethylenedioxy)-16-m-methoxyphenoxy-17,18,19,20-tetrakisnor-13-prostenoic acid ethyl ester |
| 43 | 9,9;15,15-bis-(ethylenedioxy)-16-(2,4-dichlorophenoxy)-17,18,19,20-tetrakisnor-13-prostenoic acid ethyl ester |

EXAMPLE 44

Within the course of 2 hours, 15 ml of solvent is distilled from a mixture of 1 g of 9,9-ethylenedioxy-15-oxo-13-prostenoic acid ethyl ester, 20 ml of 2-ethyl-2-methyldioxolan and 15 ml of p-toluenesulphonic acid monohydrate. The reaction product is mixed with 30 ml of saturated aqueous NaHCO$_3$ solution and extracted with diethyl ether. The organic phase is washed with water and dried over Na$_2$SO$_4$. The solvent is distilled and after chromatographic purification of the residue, 9,9;15,15-bis-(ethylenedioxy)-13-prostenoic acid ethyl ester is obtained.

IR: 1730 and 1460 cm$^{-1}$; NMR: 5.71 (q), 5.32 (d), 4.13 (q), 3.19 (m).

EXAMPLE 45

A mixture of 500 mg of 9,15-dioxo-13-prostenoic acid ethyl ester, 15 ml of dry benzene, 1 ml of ethyleneglycol and 5 mg of p-toluenesulphonic acid monohydrate is boiled for 16 hours on a water separator. After cooling, the mixture is diluted with 100 ml of diethyl and washed with aqueous NaHCO$_3$ solution and water. The organic phase is dried over Na$_2$SO$_4$ and the solvent is distilled. After chromatographic purification of the residue (silica gel/diisopropyl ether), 9,9;15,15-bis-(ethylenedioxy)-13-prostenoic acid ethyl ester is obtained.

IR: 1730 and 1460 cm$^{-1}$; NMR: 5.71 (q), 5.32 (d), 4.13 (q), 3.19 (m).

EXAMPLE 46

From a mixture 0.96 g of 9,15-dioxo-13-prostenoic acid ethyl ester, 20 ml of 2-ethyl-2-methyldioxolan and 15 ml of p-toluenesulphonic acid monohydrate, 15 ml of solvent is distilled off within the course of 2 hours. The reaction product is mixed with 30 ml of saturated aqueous NaHCO$_3$ solution and extracted with diethyl ether. The organic phase is washed with water and dried over Na$_2$SO$_4$. The solvent is dsitilled. After chromatographic purification of the residue, 9,9;15,15-bis-(ethylenedioxy)-13-prostenoic acid ethyl ester is obtained.

IR: 1730 and 1460 c, $^{-1}$; NMR: 5.71 (q), 5.32 (d), 4.13 (q), 3.19 (m).

EXAMPLES 47–51

Analogously to Example 45, from 9,15-dioxo-13-prostenoic acid ethyl ester, by boiling with an alcohol suitable as ketalising agent, in the presence of p-toluenesulphonic acid, the following compounds of formula I are obtained:

| Example | Compound of formula I |
|---|---|
| 47 | 9,9;15,15-bis-(trimethylenedioxy)-13-prostenoic acid ethyl ester |
| 48 | 9,9;15,15-bis-(2,2-dimethyl-trimethylenedioxy) 13-prostenoic acid ethyl ester |
| 49 | 9,9;15,15-bis-(propylenedioxy)-13-prostenoic acid ethyl ester |
| 50 | 9,9,15,15-tetramethoxy-13-prostenoic acid ethyl ester |
| 51 | 9,9,15,15-tetraethoxy-13-prostenoic acid ethyl ester. |

EXAMPLES 52–56

Analogously to Example 1, from 9,9-ethylenedioxy-15-oxo-13-prostenoic acid ethyl ester, by reaction with an alcohol suitable as ketalising agent, in the presence of p-toluenesulphonic acid, the following compounds of formula I are obtainable:

| Example | Compound of formula I |
|---|---|
| 52 | 9,9-ethylenedioxy-15,15-trimethylenedioxy-13-prostenoic acid ethyl ester |
| 53 | 9,9-ethylenedioxy-15,15-(2,2-dimethyltrimethylenedioxy)-13-prostenoic acid ethyl ester |
| 54 | 9,9-ethylenedioxy-15,15-propylenedioxy-13-prostenoic acid ethyl ester |
| 55 | 9,9-ethylenedioxy-15,15-dimethoxy-13-prostenoic acid ethyl ester |
| 56 | 9,9-ethylenedioxy-15,15-diethoxy-13-prostenoic acid ethyl ester |

EXAMPLES 57–61

Analogously to Example 1, from 9,9-trimethylenedioxy-15-oxo-13-prostenoic acid ethyl ester, by reaction with an alcohol suitable as ketalising agent, in the presence of p-toluenesulphonic acid, the following compounds of formula I are obtainable:

| Example | Compound of formula I |
|---|---|
| 57 | 9,9-trimethylenedioxy-15,15-ethylenedioxy-13-prostenoic acid ethyl ester |
| 58 | 9,9-trimethylenedioxy-15,15-(2,2-dimethyltrimethylenedioxy)-13-prostenoic acid ethyl ester |
| 59 | 9,9-trimethylenedioxy-15,15-propylenedioxy-13-prostenoic acid ethyl ester |
| 60 | 9,9-trimethylenedioxy-15,15-dimethoxy-13-prostenoic acid ethyl ester |
| 61 | 9,9-trimethylenedioxy-15,15-diethoxy-13-prostenoic acid ethyl ester |

EXAMPLES 62–66

Analogously to Example 1, from 9,9-diethoxy-15-oxo-13-prostenoic acid ethyl ester, by reaction with an alcohol suitable as ketalising agent, in the presence of p-toluenesulphonic acid, the following compounds of formula I are obtainable:

| Example | Compound of formula I |
|---|---|
| 62 | 9,9-diethoxy-15,15-ethylenedioxy-13-prostenoic acid ethyl ester |
| 63 | 9,9-diethoxy-15,15-trimethylenedioxy-13-prostenoic acid ethyl ester |
| 64 | 9,9-diethoxy-15,15-(2,2-dimethyl-trimethylenedioxy)-13-prostenoic acid ethyl ester |
| 65 | 9,9-diethoxy-15,15-propylenedioxy-13-prostenoic acid ethyl ester |
| 66 | 9,9-diethoxy-15,15-dimethoxy-13-prostenoic acid ethyl ester |

EXAMPLE 67

A mixture of 2 g of 9-oxo-15,15-ethylenedioxy-13-prostenoic acid methyl ester (obtainable from 7-(2-formyl-5-oxo-cyclopentyl)-heptanoic acid methyl ester by reaction with dimethyl-2,2-ethylenedioxyheptyl phosphonate in the presence of NaH), 100 ml of dry benzene, 10 ml of ethylene glycol and 0.2 g of p-toluenesulphonic acid is boiled for 12 hours on a water separator. After cooling, the mixture is diluted with 100 ml of diethyl ether and washed with aqueous NaHCO$_3$ solution and water. The organic phase is dried over Na$_2$SO$_4$ and the solvent distilled. After chromatographic purification of the residue (silica gel/diisopropyl ether), 9,9;15,15-bis-(ethylenedioxy)-13-prostenoic acid methyl ester is obtained.

EXAMPLE 68

A mixture of 1.5 g of 9-oxo-15,15-ethylenedioxy-13-prostenoic acid methyl ester, 20 ml of trimethoxymethane and 3 drops of concentrated H$_2$SO$_3$ is boiled for 6 hours. 15 ml of the solvent is distilled within 2 hours. The residue is diluted with 30 ml of diethyl ether, washed with aqueous saturated NaHCO$_3$ solution and H$_2$O and dried over MgSO$_4$. The solvent is distilled. After chromatographic purification of the residue (silica gel/diisopropyl ether), 9,9-dimethoxy-15,15-ethylenedioxy-13-prostenoic acid methyl ester is obtained.

EXAMPLE 69

A mixture of 2.6 g of 9,15-dioxo-13-prostenoic acid, 100 ml of benzene, 0.3 g of methanesulphonic acid and 20 ml of ethanol is boiled for 17 hours on a water separator. After cooling, the mixture is diluted with 100 ml of diethyl ether and washed with aqueous saturated NaHCO$_3$ solution and water. The organic phase is dried over Na$_2$SO$_4$ and the solvent is distilled. After chromatographic purification of the residue (silica gel/diisopropyl ether), 9,9;15,15-tetraethoxy-13-prostenoic acid ethyl ester is obtained.

EXAMPLE 70

(a) A mixture of 0.9 g of 9,9;15,15-bis-(ethylenedioxy)-13-prostenoic acid ethyl ester, 60 ml of dioxan, 40 ml of H₂O and 0.08 g of NaOH is boiled for 2 hours. The solvent is distilled. After recrystallization of the residue from methanol, the sodium salt of 9,9;15,15-bis-(ethylenedioxy)-13-prostenoic acid is obtained.

(b) 0.4 g of the sodium salt of 9,9;15,15-bis-(ethylenedioxy)-13-prostenoic acid is dissolved in 50 ml of distilled water. 1 drop of 1% ethanolic phenolphthalein solution is added and the solution is titrated with 0.01 N aqueous hydrochloric acid until the solution is just colored. The solution is then saturated with NaCl and extracted with diethyl ether. The organic phase is dried over MgSo₄ and the solvent is distilled. 9,9;15,15-bis-(ethylenedioxy)-13-prostenoic acid is obtained.

(c) Into 0.2 g of 9,9;15,15-bis-(ethylenedioxy)-13-prostenoic acid, ethereal diazomethane solution is dropped until a pale yellow color just remains. The organic solution is washed several times with aqueous sodium acetate solution. The organic phase is dried over MgSO₄ and the solvent distilled. As the residue, 9,9;15,15-bis-(ethylenedioxy)-13-prostenoic acid methyl ester is obtained.

The following examples concern mixtures of compounds of formula I with carrier and adjuvant materials conventional in pharmacy which can be used especially as medicaments:

EXAMPLE A: TABLETS

A mixture consisting of 30 g of the sodium salt of 9,9;15,15-bis-(ethylenedioxy)-13-prostenoic acid, 50 g of lactose, 16 g of maize starch, 2 g of cellulose powder and 2 g of magnesium stearate is pressed into tablets in the customary manner in such a way that each tablet contains 10 mg of the active material.

EXAMPLE B: DRAGEES

Tablets are pressed analogously to Example A and are subsequently coated by conventional techniques with a coating consisting of sugar, maize starch, talc and targacanth.

Analogously, there are obtainable tablets and dragees which contain one or more of the other active materials of formula I or their physiologically acceptable salts.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

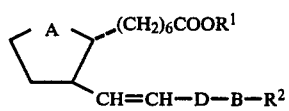

the mirror image, racemic mixtures and physiologically acceptable salts thereof
wherein A and D each independently is an open ketal group of up to 5 C-atoms or a cyclic ketal group of up to 6 C-atoms; B is —CH₂—, —CH(CH₃)—, —C(CH₃)₂—, —CH₂CH₂—, —CH(CH₃)CH₂—, —C(CH₃)₂CH₂— or —CH₂O—; R¹ is H or alkyl of 1–4 C-atoms; and R² is alkyl of 3 to 5 C-atoms, phenyl or phenyl substituted one to three times by F, Cl, CF₃, OH, OCH₃, OC₂H₅, or alkyl of 1 to 3 carbon atoms.

2. The compound of claim 1 wherein A and D are the same and are dimethoxymethylene, diethoxymethylene or 1,3-dioxolan-2,2-diyl.

3. The compound of claim 1 wherein B is methylene or ethylene and R² is butyl or pentyl.

4. The compound of claim 1 wherein B is methylene or —CH₂O— and R² is phenyl, m-chlorophenyl, p-chlorophenyl, m-fluorophenyl, m-trifluoromethylphenyl, m-methoxyphenol or p-methoxyphenyl.

5. A compound of claim 1 wherein A and D are the same and are dimethoxymethylene, diethoxymethylene or 1,3-dioxolan-2,2-diyl; B is methylene or ethylene and R² is butyl or pentyl.

6. A compound of claim 1 wherein A and D are the same and are 1,3-dioxolan-2,2-diyl; B is methylene or ethylene and R² is butyl and pentyl.

7. A compound of claim 1 wherein A and D are the same and are 1,3-dioxolan-2,2-diyl; B is methylene and R² is butyl.

8. A compound of claim 1 wherein A and D are the same and are dimethoxymethylene, diethoxymethylene or 1,3-dioxolan-2,2-diyl; B is methylene or —CH₂O— and R² is phenyl, m-chlorophenyl, p-chlorophenyl, m-fluorophenyl, m-trifluoromethylphenyl, m-methoxyphenyl or p-methoxyphenyl.

9. A compound of claim 1 wherein A and D are the same and are dimethoxymethylene, diethoxymethylene or 1,3-dioxolan-2,2-diyl; B is —CH₂O— and R² is phenyl, m-chlorophenyl, p-chlorophenyl, m-fluorophenyl, m-trifluoromethylphenyl, m-methoxyphenyl or p-methoxyphenyl.

10. A compound of claim 1 wherein A and D are the same and are 1,3-dioxolan-2,2-diyl; B is —CH₂O— and R² is phenyl, m-chlorophenyl, p-chlorophenyl, m-fluorophenyl, m-trifluoromethylphenyl, m-methoxyphenyl or p-methoxyphenyl.

11. 9,9;15,15-bis-(ethylenedioxy)-13-prostenoic acid ethyl ester, a compound of claim 1.

12. A pharmaceutical composition which comprises an amount of a compound of claim 1 effective to inhibit aggregation or adhesion of thrombocytes and a pharmaceutically acceptable carrier.

13. A method of inhibiting aggregation of adhesion of thrombocytes in mammals which comprises administering an amount of a compound of claim 1 effective for said inhibition.

* * * * *